(12) United States Patent
Kotzan et al.

(10) Patent No.: US 8,326,393 B2
(45) Date of Patent: Dec. 4, 2012

(54) LAYERED SENSOR FOR DETERMINING AN ANALYTE CONCENTRATION

(75) Inventors: Holger Kotzan, Ladenburg (DE); Gregor Bainczyk, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1114 days.

(21) Appl. No.: 12/142,437

(22) Filed: Jun. 19, 2008

(65) Prior Publication Data

US 2009/0156920 A1 Jun. 18, 2009

Related U.S. Application Data

(63) Continuation of application No. PCT/EP2006/069386, filed on Dec. 6, 2006.

(30) Foreign Application Priority Data

Dec. 19, 2005 (EP) ..................................... 05027755
Sep. 1, 2006 (DE) ......................... 10 2006 041 343

(51) Int. Cl.
*A61B 5/05* (2006.01)
(52) U.S. Cl. ........................................................ 600/345
(58) Field of Classification Search ................... 600/345
See application file for complete search history.

(56) References Cited

U.S. PATENT DOCUMENTS

| 5,286,362 | A | 2/1994 | Hoenes et al. |
| 5,509,410 | A | 4/1996 | Hill et al. |
| 5,591,139 | A | 1/1997 | Lin et al. |
| 6,560,471 | B1 | 5/2003 | Heller et al. |
| 6,695,958 | B1 | 2/2004 | Adam et al. |
| 6,892,085 | B2 | 5/2005 | McIvor et al. |
| 2003/0042137 | A1 | 3/2003 | Mao et al. |
| 2003/0078484 | A1 | 4/2003 | Schulman et al. |
| 2004/0074785 | A1 | 4/2004 | Holker et al. |
| 2004/0111017 | A1 | 6/2004 | Say et al. |
| 2005/0215871 | A1* | 9/2005 | Feldman et al. ............ 600/309 |

FOREIGN PATENT DOCUMENTS

| CA | 2050677 C | 3/1992 |
| WO | 02/06788 A2 | 1/2002 |
| WO | 2005/078424 A1 | 8/2005 |
| WO | 2005/113790 A1 | 12/2005 |

* cited by examiner

*Primary Examiner* — Jerry Lin
(74) *Attorney, Agent, or Firm* — Bose McKinney & Evans LLP

(57) ABSTRACT

An implantable sensor is provide which can be used for determining a concentration of at least one analyte in a medium, in particular a body tissue and/or a body fluid. The implantable sensor has a layered construction with at least one insulating carrier substrate and at least two electrodes which are arranged in at least two different layer planes of the implantable sensor and are electrically isolated from one another by the at least one insulating carrier substrate. The electrodes have electrode areas which face the medium when the sensor has been implanted, and are in contact with the medium over a large area and substantially uniformly, directly or via a generally analyte-permeable membrane layer.

30 Claims, 8 Drawing Sheets

LAYERED SENSOR FOR DETERMINING AN ANALYTE CONCENTRATION

CLAIM OF PRIORITY

The present application is a continuation application based on and claiming priority to PCT Application Filing, No. PCT/EP2006/069386, filed Dec. 6, 2006, which claims the priority benefit of German Application Filing No. DE 10 2006 041 343.1, filed Sep. 1, 2006, which claims the priority benefit of European Application Filing No. EP 05 027 755.7, filed Dec. 19, 2005, each of which applications are hereby incorporated by reference in their entireties.

TECHNICAL FIELD OF THE INVENTION

The present application relates to an implantable sensor for determining a concentration of at least one analyte in a sample, such as a body tissue or body fluid, to a device using such an implantable sensor, to a method of using such an implantable sensor and/or the device, and to a method for producing the implantable sensor; and more particularly to such sensors, devices and methods in the field of medical technology, and more particularly to electrochemical determination of the concentration of blood glucose, triglycerides, lactate, or other blood analytes.

BACKGROUND

For diabetics, determining the blood glucose concentrations and corresponding medication are an essential part of the course of the day. In this case, the blood glucose concentration has to be determined rapidly and simply a number of times a day (typically two to seven times) in order to be able to take corresponding medical measures, if appropriate. In many cases, medication is effected by means of automatic systems, in particular so-called insulin pumps.

In order not to restrict the diabetic's day any more than necessary, correspondingly mobile devices are often used, which should be simple to transport and handle, so that the blood glucose concentration can be measured without any problems, for example at the workplace or else during leisure time. Various mobile devices which function in part according to different measurement methods and using different diagnosis methods are commercially available at the present time. A first measurement method is based on an electrochemical measurement method. For example, a blood sample, taken from the body tissue from the patient for example by perforating a skin layer by means of a lancet, is applied to an electrode coated with enzymes and mediators. Corresponding test strips for electrochemical measurement methods of this type are described in U.S. Pat. No. 5,286,362, for example, the disclosure of which is hereby incorporated herein by reference. Other known measurement methods use optical measurement methods based for example on the fact that the substance (analyte) to be detected may react with specific detection reagents, a change in the color of the reaction mixture occurring. Systems for detecting such color reactions and thus for detecting the corresponding analytes are known from CA 2,050,677, for example, the disclosure of which is hereby incorporated herein by reference.

The detection methods described are therefore based predominantly on the fact that a patient firstly takes a corresponding sample of the body fluid to be examined (this being for example a blood sample or a urine sample) and then examines it correspondingly by means of the test device. However, this method comprises various disadvantages. Firstly, this method is extremely complicated and presupposes a plurality of handling steps. Thus, by way of example, a lancet has to be provided and tensioned, a skin layer subsequently has to be perforated by means of said lancet, a drop of blood thus produced then has to be applied to a test strip, and said test strip subsequently has to be evaluated by means of a corresponding device. For many patients, in particular older people and children, these handling steps can often be carried out only with difficulty since the patients are restricted for example in terms of their motor ability and their vision capability. Furthermore, these method steps can be carried out discretely only in a few cases, such that for example protection of the patient's privacy during a measurement at the workplace is only inadequately ensured. Moreover, incorrect operation of the measurement method can easily lead to false measured values, with in some instances fatal consequences of an incorrect medication based on the measurement results.

The prior art therefore discloses systems which can be implanted into a body tissue and which supply measured values continuously. See, for example, U.S. Pat. No. 6,892,085 and U.S. Pat. No. 5,591,139, the disclosures of which are hereby incorporated herein by reference in their entireties.

Overall, however, the implantable sensors known from the prior art are extremely complicated with regard to their construction and their production. If it is assumed that said sensors are disposable sensors that can only be used for a short time (typically approximately one week), then it becomes clear that the complicated manufacturing methods used for making the sensors known from the prior art do not satisfy such requirements made of disposable articles. See, for example, the lithographic methods disclosed by U.S. Pat. No. 5,591,139 and U.S. Pat. No. 6,892,085 which are referenced supra. However, such methods cannot be reconciled with the production of cost-effective disposable articles.

Moreover, lithographic methods, in particular the etching of metal layers that is associated with these methods, are not always as reliable as necessary for producing medical-technological products. In particular, it can happen that individual electrodes are still connected to one another by "bridges", such that the functionality of the sensors can easily be impaired or even completely prevented on account of production problems. A further disadvantage of the sensors known from the prior art, such as, for example, the sensors known from U.S. Pat. No. 6,892,085 B2 and U.S. Pat. No. 5,591,139, furthermore arises in the use of a hollow needle or capillary. In these cases, the sensors are introduced into a capillary which transports the body fluid to be examined towards the sensor. What is disadvantageous about this, however, is that the capillary makes it more difficult for the analyte solution to have unimpeded access to the electrodes. In particular, this can also give rise to local concentration corruptions which have the effect that measurement results do not correspond to the actual concentration conditions in the body fluid. In this case, complex diffusion processes and flow processes in the capillaries also play a part and contribute to the corruption.

Other prior art sensors are provided for in vivo measurement based on an electrochemical principle, having two electrodes on a carrier substrate. See, for example, US 2004/0111017, the disclosure of which is hereby incorporated by reference in its entirety. In such in vivo sensors, a working electrode coated with a detector layer for the analyte to, be detected is applied directly to the carrier substrate and covered by a covering layer. A common reference electrode and counter electrode can be applied on the opposite side of the covering layer to the working electrode and overlaps the working electrode but is isolated from the latter by the covering layer (which is necessarily to be configured in electrically insulating fashion). The analyte passes via diffusion mechanisms from the edges of the sensor to the working electrode. As an alternative, the covering layer itself can also be made analyte-permeable.

Such a sensor arrangement has various disadvantages in practice, however. One exemplary disadvantage is the fact that the covering layer must simultaneously perform two different functions which are compatible only with difficulty in terms of material technology. Thus, the covering layer must on the one hand have sufficient electrically insulating properties in order to insulate the working electrode and the counter electrode from one another. The covering layer must nevertheless enable the analyte that is to be detected to penetrate at least from the edge in order to pass to the working electrode, in order to be able to be detected electrochemically there. This diffusion must able to take place to a sufficient extent in order to be able to provide sufficient responsive electrical currents for a measurement of the analyte concentration (signal response). The simultaneous permeability for diffusion and sufficient insulation capability make stringent requirements of the material properties, however. One solution for solving this problem is a structural configuration of the sensor in which diffusion channels enabling the analyte to penetrate are provided in the layer construction. However, this structure is technically so complicated that the production advantages which can be afforded by a layer construction are virtually completely given away again.

It is an object of the invention, therefore, to provide a sensor for determining a concentration of at least one analyte in a medium, which sensor can be produced simply and cost-effectively by means of a reliable production method and if possible avoids the disadvantages of the sensors and methods known from the prior art. In particular, the sensor is intended to be implantable and to ensure sufficient signal swings.

SUMMARY

This object and others that will be appreciated by a person of ordinary skill in the art have been achieved according to the embodiments of the present invention disclosed herein. In one embodiment, the present invention comprises an implantable sensor for determining a concentration of at least one analyte in a medium, in particular in a body tissue and/or a body fluid. The analyte may be for example glucose, triglycerides, lactate, hormones or other analytes which are important particularly in medicine. As an alternative or in addition, however, the sensor can also be used for measuring other types of analytes. In one embodiment, the sensor is based on the use of an electrochemical measurement method.

A basic concept of the invention comprises using a suitable layered construction to solve the above-described problem that, on the one hand, electrical insulation of the electrodes from one another is necessary and, on the other hand, the electrodes should be as freely accessible as possible for the at least one analyte. Accordingly, an implantable sensor is configured in such a way that at least two electrodes are applied on an electrically insulating carrier substrate in at least two different layer planes, for example on a front side and a rear side and/or in different step planes. The at least two electrodes are electrically isolated from one another by the at least one carrier substrate.

Furthermore, the at least two electrodes have electrode areas, that is to say active surfaces, at which electrochemical reactions (redox reactions) can proceed. According to the invention, in order to obtain the maximum signal response, these at least two electrode areas face the medium when the sensor has been implanted into the medium, and are in contact with the medium substantially uniformly, directly or via an analyte-permeable membrane layer. The intention is not only to enable analyte to penetrate via the sensor edge, but also to enable contact to take place perpendicular to the electrode areas from the medium. Thus, analyte is generally unimpeded to the entire electrode areas. Nevertheless, slight restrictions of accessibility can be accepted here, for example by slight coverings of the electrode areas, for example of not more than 10% of the electrode areas.

The configuration according to the invention has therefore separated and thus optimized the two functions which are realized by one and the same layer, namely the covering layer between the overlapping electrodes. The electrical insulation is now realized by the at least one insulating carrier substrate and the spatial arrangement of the at least two electrodes. The accessibility of the electrodes to the medium or the analyte is ensured by virtue of the fact that the at least two electrodes no longer overlap completely or partially, rather they are arranged for example alongside one another and are freely in contact with the medium. In this case, as described above, "freely" should be understood not to be limited to completely free accessibility but includes contact via a membrane layer which is generally permeable to the at least one analyte. An appropriate membrane layer can ensure, for example, the biocompatibility and thus the implantability of the sensor (see below). Such a membrane layer, which is configured for example to prevent diffusion of electrode material or parts thereof into the medium (e.g. cell tissue), or to provide for contact of the at least one electrode with the medium, does not have to satisfy any requirements whatsoever in terms of the electrical insulation effect. Therefore, as long as the biocompatibility requirements are met, the membrane layer can be made as thin as desired, for example. Overall, therefore, in this case the membrane layer and the at least one carrier substrate together perform the tasks which are fulfilled by the covering layer alone, if appropriate in interaction with the complex diffusion channels.

The implantable sensor can be advantageously developed in various ways according to the invention. In this case, the advantageous developments described can be used individually or in combination.

In one embodiment, the at least two electrodes comprise at least one working electrode and at least one further electrode, such as a counter electrode and/or a reference electrode. In this case, the at least one working electrode and the at least one further electrode are arranged in different planes of the layered construction. The analyte concentration is then measured after wetting by the medium or after implantation of the sensor by means of amperometric measurement between the at least two electrodes (e.g., working electrode and counter electrode), such as by means of a DC voltage. A reference electrode for currentless measurement of the working electrode potential can additionally be used.

In this case, "in different-planes" should be understood to mean generally that at least one insulating carrier substrate is arranged between the at least two electrodes, such that at least two of the at least two electrodes are isolated by the insulating carrier substrate. Consequently, in contrast to the prior art described above, the "third dimension" is concomitantly used in this construction of an implantable sensor.

Although the prior art discloses electrochemical cells, for example electrochemical microcells, in which electrodes are arranged on opposite sides of a carrier, there the carrier is an electrolyte material, in particular a solid electrolyte. In contrast thereto, the at least one insulating carrier substrate of the electrochemical sensor according to the present invention comprises an electrically non-conductive material. This is intended to mean generally that if a voltage of up to approximately 1-2 volts is applied to two electrodes arranged on opposite sides of the at least one insulating carrier substrate, currents of not more than one milliampere, preferably of not more than 100 microamperes, and particularly preferably of not more than 10 microamperes, flow. This generally ensures that the measurement current on account of the electrochemical measurement method is considerably greater than the current which flows through the at least one insulating carrier substrate despite the insulating properties of the electrically non-conductive material of the at least one insulating carrier substrate.

Furthermore, the at least one carrier substrate can also additionally be configured in such a way that diffusion of the at least one analyte through the at least one carrier substrate is not possible or is greatly impeded. In this respect, the at least one carrier substrate also differs significantly with regard to the material requirements from the covering layer used in prior art sensors such that a larger number of suitable materials are available and can be used.

For making contact with the at least two electrodes, the embodiments of an implantable sensor of the present invention can furthermore have one or a plurality of electrode contact layers. The latter may involve for example electrically conductive layers, e.g. metallic layers, in particular layers having carbon, graphite, gold, silver, platinum and/or aluminum. Multilayered constructions are also possible. Organic conductor materials are also appropriate as electrode contact layers that make electrical contact.

Since the at least two electrodes are arranged in at least two layer planes of the layer construction of the sensor, it is now possible for the at least two electrodes and/or the at least two electrode contact layers to extend substantially over the entire width of the at least one insulating carrier substrate. Thus, the insulating carrier substrate may in particular have a longitudinal extent and also a width and a length, the electrode contact layers and/or the electrodes substantially extending from one edge of the insulating carrier substrate to the other. In this case, "substantially" can be understood to mean a covering of the insulating carrier substrate by the electrode contact layer of at least 80%, and in certain embodiments at least 95% and up to 100%. Therefore, on account of the separation by the construction in different planes, a structuring of the electrodes and/or electrode contact layers is no longer necessary, such that complex lithographic structuring methods or laser structuring methods (e.g. laser ablation) can be dispensed with. The advantages of this possibility will become clear below when a possible method for the production of the implantable sensor is described in detail.

Furthermore, the implantable sensor can have at least one insulator layer which covers and preferably electrically insulates the at least two electrode contact layers at least partly with respect to the medium, in particular the body tissue and/or the body fluid. In this case, the for example at least two electrode contact layers can be partly covered by the at least two electrodes, the uncovered regions being covered (e.g. subsequently) by the at least one insulator layer. Self-adhesive film layers can be used as insulator layers. In this way, by way of example, the at least one insulator layer prevents undesirable electrochemical reactions, for example electrolysis reactions with gas formation, from proceeding at the uncovered regions of the electrode contact layers upon contact with the surrounding medium and application of a voltage.

Even further layers not mentioned can also be provided alongside the layer construction described above. Thus, the at least one insulating carrier substrate may initially be a carrier substrate composed of, for example, a plastic, ceramic or paper material. As an alternative or in addition, the at least one carrier substrate itself may already have a multilayered construction, for example a substrate material coated with further layers. Thus, by way of example, substrate materials with additional barrier layers can be used. It is particularly preferred if the at least one insulating carrier substrate comprises a polymer, such as an insulating polymer, e.g. a polyester. Further layers, for example conductive or electrically insulating layers, can also be introduced between the at least one insulating carrier substrates and the at least two electrode contact layers and/or the at least two electrodes.

The implantable sensor in accordance with the embodiments described herein can be inserted for example into a canula. In one embodiment, the implantable sensor can be introduced into the medium, in particular the body tissue, directly, that is to say without a surrounding canula or capillary. This ensures that body fluid can wash freely around the electrodes arranged in the at least two planes. For this purpose, the implantable sensor, as already described above, can have at least one membrane layer that completely or partly encloses the layer construction. Said at least one membrane layer advantageously has, at least in part, a permeability to the at least one analyte that is to be detected. By way of example, the at least one membrane layer can have a permeability to glucose, lactate, triglycerides and/or further analytes. In this case, however, the at least one membrane layer should advantageously be impermeable to auxiliary chemicals used in the electrochemical measurement method, for example to enzymes used which are applied to one or more of the electrodes. By way of example, glucose oxidase may be involved in this electrochemical method. Consequently, the membrane layer also ensures that said auxiliary chemicals, which are of considerable toxicity in some instances (e.g. glucose oxidase constitutes a cell poison), cannot pass into the body tissue and cause damage there.

The at least one membrane layer can enclose for example the region in which the electrodes are applied. By way of example, the at least one membrane layer can have a polyurethane. A multilayered membrane layer construction is also possible. By way of example, wet-chemical methods, e.g. dipping methods or spraying methods, or else other known coating methods can be used for applying the polyurethane.

The at least two electrodes can be configured in various ways. In particular, the at least two electrodes, as described above, can comprise at least one working electrode and at least one further electrode having at least one counter electrode and at least one reference electrode. In particular, the at least one counter electrode should have an opposite redox behavior to a redox behavior of the at least one working electrode. A counter electrode and a reference electrode can also be formed as a common electrode. In one embodiment, they are formed as a common electrode whose area is greater than the area of the at least one working electrode. The prior art discloses examples for the use of electrode materials for electrochemical measurement methods. Thus, by way of example, electrodes can be coated with enzymes or other chemical adjuvants which are specific to the analyte to be detected. By way of example, for detecting glucose it is possible to use glucose oxidase (GOD) which converts glucose into gluconolactone. The charge carriers released in the process are detected. In order to enable this detection, the overvoltage-reducing materials are used, which serve as it were as "charge mediators" between the medium and the electrodes.

Many of said overvoltage-reducing materials are harmful to health, however. In particular, these so-called mediators have proved to be toxic, such that it is necessary to immobilize said overvoltage-reducing materials for use in implantable sensors in many cases. By way of example, a covalent bonding to the electrode and/or a layer of the electrode, for example a metal layer, can be effected for immobilization purposes. In particular, this technique can be used for immobilizing mediators. A second possibility comprises integrating the overvoltage-reducing material into an insoluble layer that is insoluble in the fluid, in particular the body fluid, surrounding the implantable sensor in the implanted state. This can be effected for example when using manganese dioxide, which is applied as a paste to the electrode and is then insoluble after drying.

Nitrosoanilines, hexacyanoferrate, ferrocenes or other known mediators can be used, for example, as mediators. Other materials can also be used besides manganese dioxide.

Besides the described configuration of the at least one working electrode, the at least one reference electrode and/or the at least one counter electrode can also be configured in various ways. In embodiments comprising at least a reference electrode, the reference electrode should comprise an electron system with an electrochemical potential that does not change, or changes only insignificantly, in a working range of the implantable sensor. Thus, by way of example, given a typical voltage loading (that is to say a voltage between working electrode and reference electrode) of typically about 300-500 millivolts, e.g. about 450 millivolts, the electrochemical potential of the at least one, reference electrode should typically change by not more than about 1 millivolt. In one embodiment, the electrochemical potential of the at least one reference electrode changes by not more than about 1 microvolt. This stability ensures that the reference electrode acts as an actual reference with the potential of which the electrochemical potential of the at least one working electrode can be compared.

In principle, a multiplicity of materials and/or material combinations can be used for the reference electrode. A silver/silver chloride (Ag/AgCl) electrode system has proved to be particularly useful in this case. Other electrode systems can also be used in principle, but are less common, such as e.g. $HgCl_2$ electrode systems.

The at least one counter electrode can also be configured in a large number of different ways. In this case, however, it should be ensured that the at least one counter electrode has an opposite redox behavior to a redox behavior of the at least one working electrode with respect to the surrounding fluid. Therefore, if an oxidation takes place at the working electrode, a reduction should take place at the counter electrode, and vice versa. In principle, pure metals can be used as counter electrodes, such as platinum for example. This has the disadvantage, however, that a gas formation, for example a formation of hydrogen or oxygen, typically occurs at metal electrodes of this type. A gas formation of this type is undesirable, however, when the sensor has been implanted in the body tissue. In this respect, it is once again advantageous here, too, if an electrode system, in particular a redox electrode system, is used in which gas formation is avoided. In particular, a Ag/AgCl electrode system can again be used here as well. By way of example, AgCl is reduced in this case. It is evident from this that the counter electrode is consumed during operation of the sensor. If the counter electrode has been fully consumed, gas formation once again often takes place, such that the implantable sensor generally has a limited lifetime in operation. Accordingly, in one embodiment, the at least one counter electrode is made considerably larger than the at least one working electrode in terms of its area.

The way in which the electrodes are applied to the electrode contact layers can be effected in various ways, depending on the electrode material used. If, by way of example, pure metals are used as electrode materials, then it is possible, for example, to use film methods (e.g. lamination) or wet-chemical methods, physical application methods (physical vapor deposition, PVD, e.g. vapor deposition or sputtering) or else chemical application methods (chemical vapor deposition, CVD). Manganese dioxide ($MnO_2$/C) can be applied for example as a coating, for example as a paste coating. In this case, various coating methods known to the person skilled in the art can be used, for example screen printing, blade coating, nozzle coating or the like. In this case, by way of example, an enzyme can already be mixed with the paste, such that enzyme and manganese dioxide can be applied in one step. As an alternative, it is also possible firstly for manganese dioxide to be applied, whereupon in a subsequent step the enzyme, for example glucose oxidase (GOD), is e.g. dispensed thereon or applied in another wet-chemical step. The other electrodes are also applied correspondingly. Typical electrode layer thicknesses lie in the range of about 10 micrometers, but can also extend to the range of a hundred to a few hundred micrometers. Thinner electrode layers may also by used.

According to embodiments of the invention, the implantable sensor and/or a device which contains the implantable sensor can be used for a continuous determination of a concentration of at least one analyte in the body tissue and/or a body fluid. In this case, "continuous" can be understood for example to mean that analyte concentrations are determined over a specific measurement period, for example one week, at regular intervals (e.g. every five minutes or every hour) or else permanently, i.e. with a temporal resolution which is only limited by the temporal resolution of a measuring device.

One problem, however, in the case of a continuous measurement consists in a possible drift of the device and/or of the sensor over the measurement period. A continuous measurement is usually effected by firstly carrying out a reference measurement by means of a "conventional" measurement method (e.g. taking a drop of blood and measuring analyte concentration in the drop of blood), said reference measurement then being trimmed with the measured value supplied by the implanted sensor. A measurement then follows over the measurement period taking the initial reference measured value as a basis. However, if the property of the implantable sensor changes, for example on account of a drift of an electrochemical potential, in particular of the electrochemical potential of one of the at least one working electrode and/or of the at least one reference electrode, then this measurement is erroneous and subject to a drift.

It has been shown in practice that in particular the at least one membrane layer and the electrode material used for the at least one working electrode represent critical points with regard to drift. The use of a manganese dioxide paste, in particular a manganese dioxide paste admixed with an enzyme (e.g. glucose oxidase), which is applied and subsequently dried, has proved to be advantageous in this case since this selection minimizes a drift. Moreover, the use of the advantageous polyurethane membrane described additionally minimizes the drift.

The implantable sensor according to the embodiments of the invention can furthermore be provided with an insertion tip for inserting the implantable sensor into the medium, in particular into a fatty tissue (e.g. into an interstitial fatty tissue). In this case, by way of example, the topmost skin layer can be penetrated and the sensor can be pushed at least partly under the dermis.

An insertion tip can be configured in various ways. As mentioned above and also known from the prior art, it is possible to use canulas, for example. In particular, however, it is preferred according to the invention if the sensor itself that is to say for example the layer construction itself, has an insertion tip of this type.

The problem with previous sensors, however, is that they are usually designed to be very thin and wide. As a result, the layer construction flexes upon insertion, such that the force required for inserting the sensor-cannot be transmitted via the sensor and that the latter bends beforehand. However, the sensor according to embodiments of the invention, in which the electrode contact layers are preferably applied over a large area and do not have to be structured, enables a construction having a high aspect ratio. In this case, an aspect ratio should be understood to mean the ratio between the height and the width of the insulating carrier substrate and/or of the entire layer construction. Thus, by way of example, insulating carrier substrates and/or layer-constructions can be used in which said aspect ratio, which is referred to hereinafter as k, is at least about 0.3, and in certain other embodiments k is at least about 0.5, and in yet others k is at least about 0.9.

If it were desired to achieve such aspect ratios with conventional sensors, in which the electrode contact layers are structured, it would be necessary, since structured electrodes presuppose a large width of the insulating carrier substrate, also to use very thick sensors. This in turn means a large cross section of the insertion channel of the sensor. The construction according to the invention, in which a high aspect ratio is achieved whilst simultaneously minimizing the insertion area, avoids this disadvantage.

In one embodiment, the layered construction of the sensor according to the invention is a stepped layer construction. In this case, at least two insulating carrier substrates should be present, at least two of said insulating carrier substrates forming a step. In other embodiments, the step is formed in the longitudinal extent direction of the implantable sensor (that is to say in the insertion direction). For this purpose, by way of example, one of the at least two insulating carrier substrates can be made shorter than a second one of the insulating carrier substrates, whereby a step arises preferably at the tip of the sensor or in the vicinity of the tip. As a result, it is possible for example to form three electrodes provided in three different layer planes. By way of example, at least one of said electrodes can be provided in the plane of the step, in particular at the step itself. In this way, the sandwich structure already described above is extended further into the third dimension.

In practice, the particular properties and the particularly simple production, in particular two-layered constructions or the combinations thereof, have proved worthwhile, in which case, however, the layered, constructions illustrated can be extended, if appropriate, by additional layers not mentioned below. On the one hand, a stepped layer construction is appropriate, in which at least two insulating carrier substrates form at least one step. On the other hand, alternatively or additionally, a so-called "back-to-back" construction can be used, in which at least two electrodes are arranged on opposite sides of the at least one carrier substrate and have oppositely directed electrode areas facing the medium.

In particular, the stepped construction can be configured in such a way that at least one electrode is arranged in the plane of the at least one step, and that the at least one electrode arranged in the plane of the at least one step and at least one further electrode have parallel, equidirectional electrode areas. Furthermore, two steps can be provided, equidirectional electrodes being provided in the two planes of the two steps. In this case, "equidirectional" should be understood to mean that the electrode areas, that is to say the areas facing the medium, point in the same direction.

The stepped construction can be combined with a "back-to-back" construction in such a way that in addition to the step construction described in one of the configurations described, at least one further electrode is provided which is arranged on a side of the at least one carrier substrate that is remote from the at least one step, and is oriented with its electrode area opposite to the step.

The back-to-back construction can be realized, by itself or in combination, for example by providing at least one carrier substrate embedded between a first electrode contact layer and a second electrode contact layer. It is then possible for at least one first electrode to be provided on that side of the first electrode contact layer which is remote from the at least one carrier substrate, and for at least one second electrode to be provided on that side of the second electrode contact layer which is remote from the carrier substrate.

A device for determining a concentration of at least one analyte in a medium, in particular a body tissue and/or a body fluid, is furthermore proposed. The device according to one embodiment of the invention comprises at least one implantable sensor in accordance with the above description of the possible configurations. Furthermore, the at least one device comprises at least one voltage measuring device for measuring a voltage between the at least one working electrode and the at least one reference electrode. At least one current measuring device for measuring a current between the at least one counter electrode and the at least one working electrode can furthermore be provided. In addition, the device can furthermore comprise a control device configured for controlling the current between the at least one counter electrode and the at least one working electrode in such a way that the voltage measured between the at least one working electrode and the at least one reference electrode is generally equal to a predetermined desired voltage. Further methods and devices for determining an electrochemical potential difference between the at least one working electrode and the at least one counter electrode and also a concrete electronic configuration of circuits of this type are known to the person skilled in the art.

The sensor according to the embodiments of the present invention described can be used for example for a continuous determination of a concentration of at least one analyte in the body tissue and/or a body fluid. For this purpose, by way of example, the sensor according to the invention can be implanted, e.g. as part of the device according to the invention in one of the configurations described, by insertion into the body tissue. The sensor can then be afforded a certain time within which an (at least approximate) equilibrium is established in the region of the sensor and the surrounding body tissue. By way of example, a swelling of individual or all layers of the sensor may take place during this time, which may last e.g. one hour. The patient can subsequently carry out a calibration measurement in which, as described above, an analyte concentration in the body fluid, for example a glucose concentration in a drop of blood, is determined by means of a conventional method. The data determined in this case are communicated to the device according to the embodiments of the invention, for example by manual inputting or else by electronic data transfer (e.g. by means of a cable or a wireless connection). As a result, a calibration point is made available to the device, and the device according to the embodiments of the invention can trim the measured values input relative to measured values supplied by the implanted sensor. Afterwards, the implanted sensor and the device according to the embodiments of the invention can be used for example over a period of one week, a measurement being effected for example every five minutes or else in uninterrupted fashion (see above). The measured values determined by the device according to the embodiments of the invention can be output to the patient, for example, or they can also be made available to other systems, for example medication systems. Thus, by way of example, the device according to the embodiments of the invention can be connected directly to an insulin pump that adapts an insulin dose to the blood glucose concentrations measured. After the measurement time has elapsed, the entire device can be exchanged, or else just the sensor according to the invention can be exchanged for a new, unspent sensor.

A method for producing an implantable sensor, in particular an implantable sensor in accordance with the above description, which is suitable for determining an analytic concentration in a medium, in particular in body tissue and/or a body fluid, is furthermore proposed. In one embodiment, the method comprises the steps described below, in which case the steps do not necessarily have to be carried out in the following order given. Moreover, various method steps can be repeated or carried out in parallel, and additional method steps not presented can be carried out.

In one embodiment of the method, a layered construction is produced, the layered construction comprising two electrode contact layers, such as two metal layers, which are applied over a large area in at least two different layer planes to at least one carrier film comprising at least one insulating material. By way of example, the materials described above can be used for the metal layers and the at least one carrier film. Furthermore, at least two electrodes are applied to the at least two electrode contact layers, it being possible once again to use the materials described above. The layered construction is subsequently cut into sensor strips, such as by means of a precision cutting method.

In contrast to the prior art, therefore, in the method according to the invention, electrode contact layers are applied over a large area and in at least two different layer planes. An additional structuring of the at least two electrode contact layers is typically not effected. Complex lithographic structuring methods can be avoided in this case. The electrode contact layers and thus also the electrodes are nevertheless electrically isolated from one another because they are arranged in different layer planes.

Furthermore, in the cutting step it is possible to use precision cutting methods that have been perfected in the art in the meantime, with cut widths (i.e. minimum width of the strips produced by the precision cutting method) of preferably less than 1 mm. In contrast to the prior art, however, these cutting methods now do not have to be oriented to the already structured electrode layers, which was necessary in methods which are known from the prior art and in which the electrodes are generally structured lithographically. Thus, in conventional methods, it was necessary firstly to effect a structuring of the electrodes, followed by a precision orientation of a cutting tool to the already structured electrodes, followed by a cutting method. In the method claimed here, however, this initial orientation can be omitted since the first cut does not have to be positioned, or only has to be positioned insignificantly, on account of the electrode contact layers structured over a large area.

Various layer technologies can be used in the method according to the invention. Thus, by way of example, it is possible to use lamination methods, in particular for the layer-by-layer application of the carrier films, of metal layers and/or insulator layers (e.g. adhesive films). Various lamination methods are known to the person skilled in the art. In this case, it is also possible to use reel-to-reel film methods. Furthermore, in particular for the application of organic thin films or metallic thin films, it is also possible to use physical methods (e.g. physical vapor deposition, PVD) and/or chemical methods (chemical vapor deposition, CVD) and/or wet-chemical coating methods. In particular the reel-to-reel film methods described ensure that the method according to the invention, in particular for producing the implantable sensor according to the invention, is extremely cost-effective and reliable in comparison with methods known in the prior art. Carrier films, metallic films, organic layers and/or insulator layers can be applied in this way. In particular, the two particularly preferred layer constructions described above with one carrier film or two carrier films (step construction) can also be realized by means of the method according to the invention in this way.

The implantable sensor according to the embodiments of the invention, the device, the use and the production method according to the invention in one of the configurations described afford a series of advantages, which have already been described in part, over devices and methods known from the prior art. In particular, it is possible to realize a geometrical arrangement on two opposite sides (front and rear sides) of an insulating carrier substrate, e.g. of an insulating carrier substrate composed of plastic. By virtue of new cutting methods with a reduced cut width, it is possible to apply the electrode spacings with an order of magnitude comparable to that in the case of an arrangement of a planar area. The electrochemical behavior of the sensors according to the invention is accordingly not adversely influenced by the arrangement on the front and rear sides of a substrate.

Furthermore, the production method described is extremely cost-effective and can dispense with complex lithographic structuring methods or laser ablation. The electrode areas are defined solely by cutting and lamination processes, and continuous, cost-effective manufacturing methods can be used.

A complicated positioning method for positioning the individual electrodes can be dispensed with. This is advantageous particularly in the case of miniaturized sensors (with a resultant small, that is to say less painful insertion channel) having widths of less than 1 millimeter. Furthermore, the sensors described can be used both in physiological solutions with a high electrolyte content and in: solutions with a low electrolyte content.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
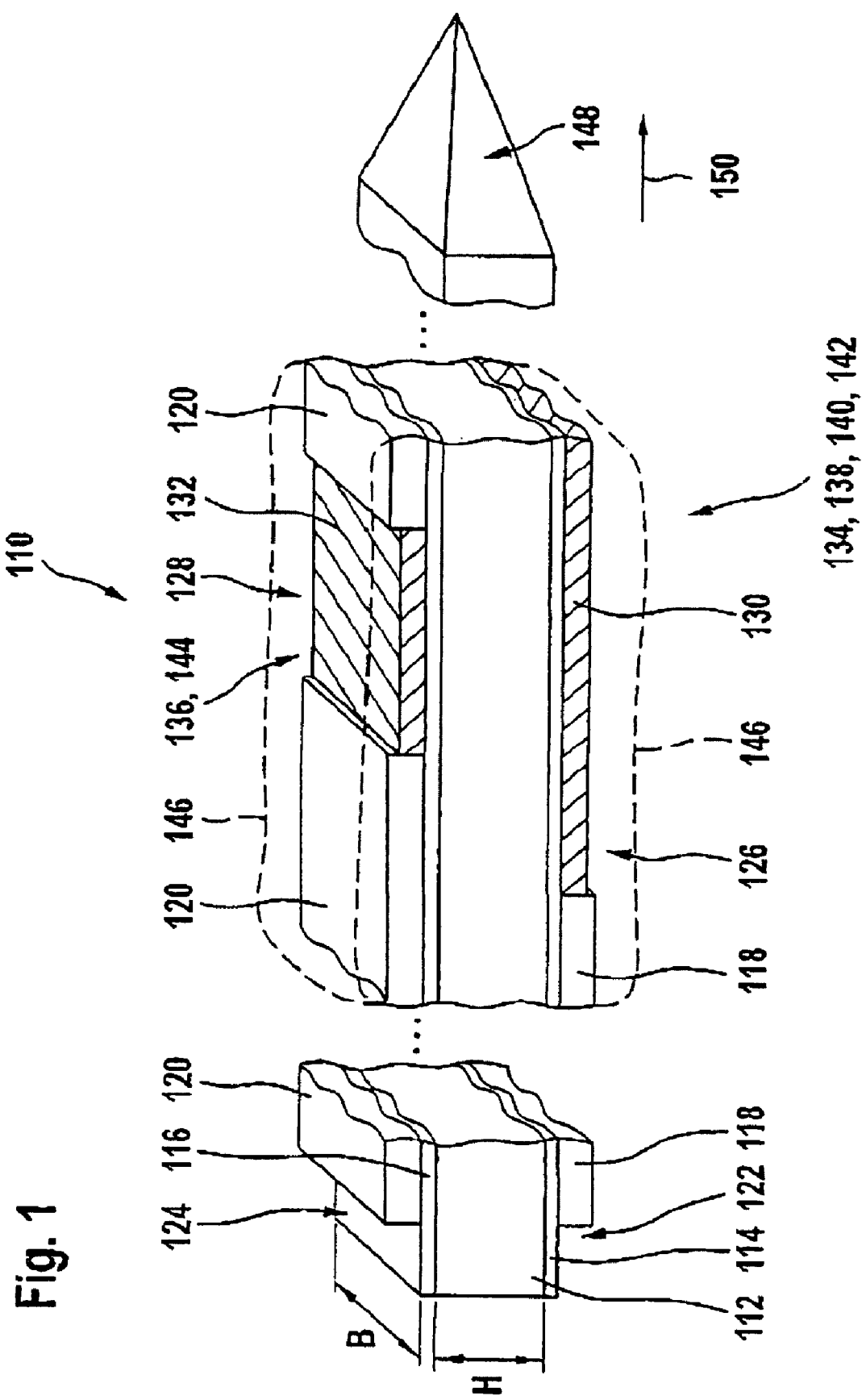
FIG. 1 shows a perspective schematic illustration of a first exemplary embodiment of an implantable sensor according to the invention.

FIG. 1 illustrates a first exemplary embodiment of an implantable sensor 110 according to the invention for determining a glucose concentration in a body fluid. The implantable sensor 110 has an insulating carrier substrate 112, which may comprise a non-conductive polyester. The insulating carrier substrate 112 has a height H of typically about 0.8 to about 1 millimeter, but other heights are also possible, in the general range of between about 0.2 and about 2 millimeters. In one embodiment, the insulating carrier substrate 112 has a width B in the region of about 1 millimeter. Consequently, an aspect ratio H/B (also represented as "k") of approximately 0.8 results in this exemplary embodiment. In other embodiments, other widths B are also possible, such as widths of between about 0.3 millimeter and about 2 millimeters. In yet other embodiments, the aspect ratio is selected to be in the region of about 1.0, and in other embodiments it is selected to be at least about 0.3, in which case the reciprocal aspect ratio (that is to say 1/k) should also be at least (0.3. This extent of the aspect ratio ensures a high stability of the implantable sensor 110.

The insulating carrier substrate 112 is coated on one side with a first electrode contact layer 114 and a second electrode contact layer 116 arranged on the opposite side. This may involve for example a film or some other layer of a metal, such as gold, silver, platinum and/or aluminum, for example, which is laminated for example onto the insulating carrier substrate 112. The electrode contact layers 114, 116 are applied to the insulating carrier substrate 112 over a large area. As shown, they extend substantially over the width B of the insulating carrier substrate 112.

A respective insulator layer 118, 120 in the form of a film layer, which in one embodiment is self-adhesive, is applied to the electrode contact layers 114, 116. Said insulator layers 118, 120 end at the left-hand end of the implantable sensor 110 in FIG. 1 before the end of the insulating carrier substrate 112, in such a way that the first electrode contact layer 114 and the second electrode contact layer 116 are uncovered in this region and form electrical contacts 122, 124. Electrical contact can be made with the electrode contact layers 114, 116 via said electrical contacts 122, 124, for example by spring contacts being applied to said electrical contacts 122, 124, or by means of other contact means, for example electrical terminals or the like.

According to one embodiment, approximately 1 to 2-centimeters away from the electrical contacts 122, 124, the insulator layers 118, 120 have openings 126, 128. In the embodiment of FIG. 1, the upper opening 128 is configured in the form of a window, whereas the lower opening 126: is configured: in such a way that the insulator layer 118 ends here. Other configurations of the openings 126, 128 are also conceivable here. In the region of said openings 126, 128, a first electrode system 130 is introduced into the opening 126 and a second electrode system 132 is introduced into the opening 128, in such a way that said electrode systems 130, 132 bear on or are otherwise supported by the electrode contact layers 114, 116. In these regions, therefore, the electrode systems 130, 132 together with the electrode contact layers 114, 116 form a first electrode 134 and a second electrode 136. In this case, in the exemplary embodiment illustrated here, the first electrode system 130 comprises a Ag/AgCl coating, whereas the second electrode system 132 comprises a $MnO_2/C$ (manganese dioxide) layer, mixed with an enzyme such as glucose oxidase (GOD).

In this exemplary embodiment, the first electrode 134 functions as a common electrode 138 and realizes the functions of counter electrode 140 and reference electrode 142. The second electrode 136 acts as a working electrode 144 in this exemplary embodiment.

In the embodiment shown in FIG. 1, the implantable sensor is encapsulated with a membrane layer 146 composed of polyurethane in the region of the electrodes 134, 136. In this exemplary embodiment, said membrane layer 146 is impermeable to the enzyme glucose oxidase, but is at least partly permeable to glucose, in which case, by way of example, diffusion of glucose can, be inhibited by the membrane layer 146. Electrical current limiting, for example, can be realized by means of this diffusion-inhibiting effect.

In other embodiments, a layered construction could also be realized in which only the working electrode 144, but not the counter electrode 140 and/or the reference electrode 142 are covered with the glucose-diffusion-inhibiting membrane layer 146. The advantage of such an arrangement in which only the working electrode 144 is covered with the membrane layer 146 is that this arrangement has a lower electrical resistance between the electrodes 140 and respectively 142 and the surrounding electrolyte. Particularly in the case of the reference electrode 142, this reduced electrical resistance becomes apparent by virtue of an increased interference immunity with respect to external electrical influences.

In yet other embodiments, different membrane layers 146 can be used for the electrodes 144, 142 and 140, or membrane layers which are composed, of a plurality of individual layers having a different functionality. Thus, by way of example, firstly the working electrode 144 could be coated with a membrane layer 146 having diffusion-inhibiting properties for glucose and an impermeability to glucose oxidase, whereas the counter electrode 140 and the reference electrode 142 remain uncoated. Afterwards, the implantable sensor 110 (completely or partly, i.e. for example in the region of the electrodes 140, 142, 144) could be coated with a further membrane layer 146, which has biocompatible properties but no or only reduced diffusion-inhibiting properties and which only serves as an outer protective layer. In this case, therefore, the membrane layer 146 would be constructed in two layers in the region of the working electrode 144, but only in one layer in the region of the counter electrode 140 and the reference electrode 142. Further possibilities for the composition of the membrane layer 146 are also conceivable.

Furthermore, in accordance with the exemplary embodiment in FIG. 1, an insertion tip 148 is provided with the implantable sensor 110. Said insertion tip 148 can be configured for example in one piece with the insulating carrier substrate 112, or an insertion tip 148 fitted separately to the insulating carrier substrate 112 may also be involved.

Figure 3A:
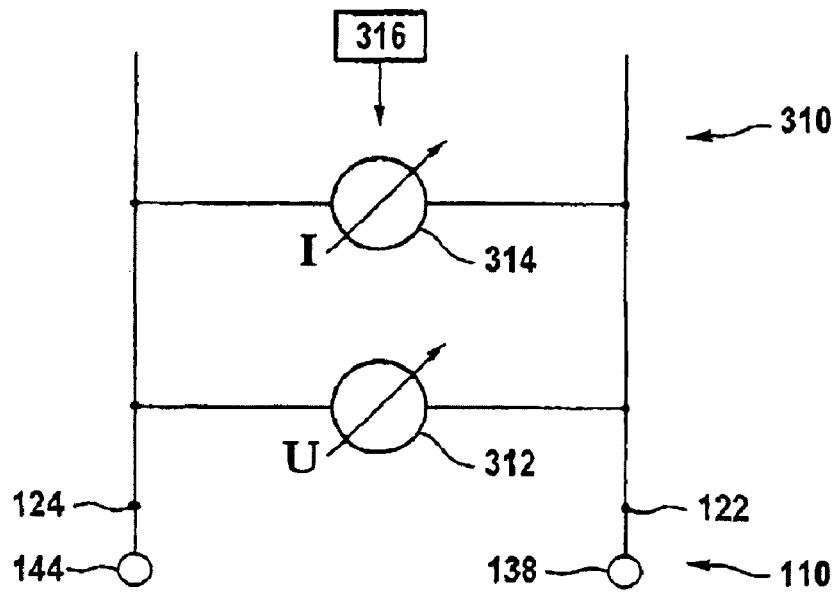
FIG. 3A shows a schematic illustration of an embodiment of a device according to the invention for determining a concentration of at least one analyte using a sensor in accordance with FIG. 1.

FIG. 3A schematically-illustrates a device 310 for determining a concentration of blood glucose using the sensor 110 in accordance with the exemplary embodiment in FIG. 1. In this case, the sensor 110 is symbolized only symbolically here by indication of the working electrode 144 and the common electrode 138. The device 310 has a voltage measuring device 312, which can be used to measure an electrochemical potential difference (voltage) between the working electrode 144 and the common electrode 138. Furthermore; the device 310 has a current measuring device 314, which can be used to measure a current flow between the working electrode 144 and the common electrode 138. Finally, a control device 316 is provided, which controls the current flowing between working electrode 144 and common electrode 138 in such a way that the voltage measured between working electrode 144 and common electrode 138 corresponds to a predetermined desired voltage. For this purpose, the control device 316 can have a dedicated voltage source, for example, which is variable. From the necessary settings of this additional voltage source of the control device 316, it is then possible to deduce for example the electrochemical potential difference between working electrodes 144 and common electrode 138.

The parts of the device 310 can be spatially separate from one another. Thus, the sensor 110 can be implanted for example partly or completely into a body tissue, whereas the rest of the device 310 is accommodated outside the body tissue, for example on the skin surface or in a separate device. Corresponding lines then lead from the current measuring device 314 and the voltage measuring device 312 to the electrical contacts 122, 124 of the sensor 110.

Figure 4:
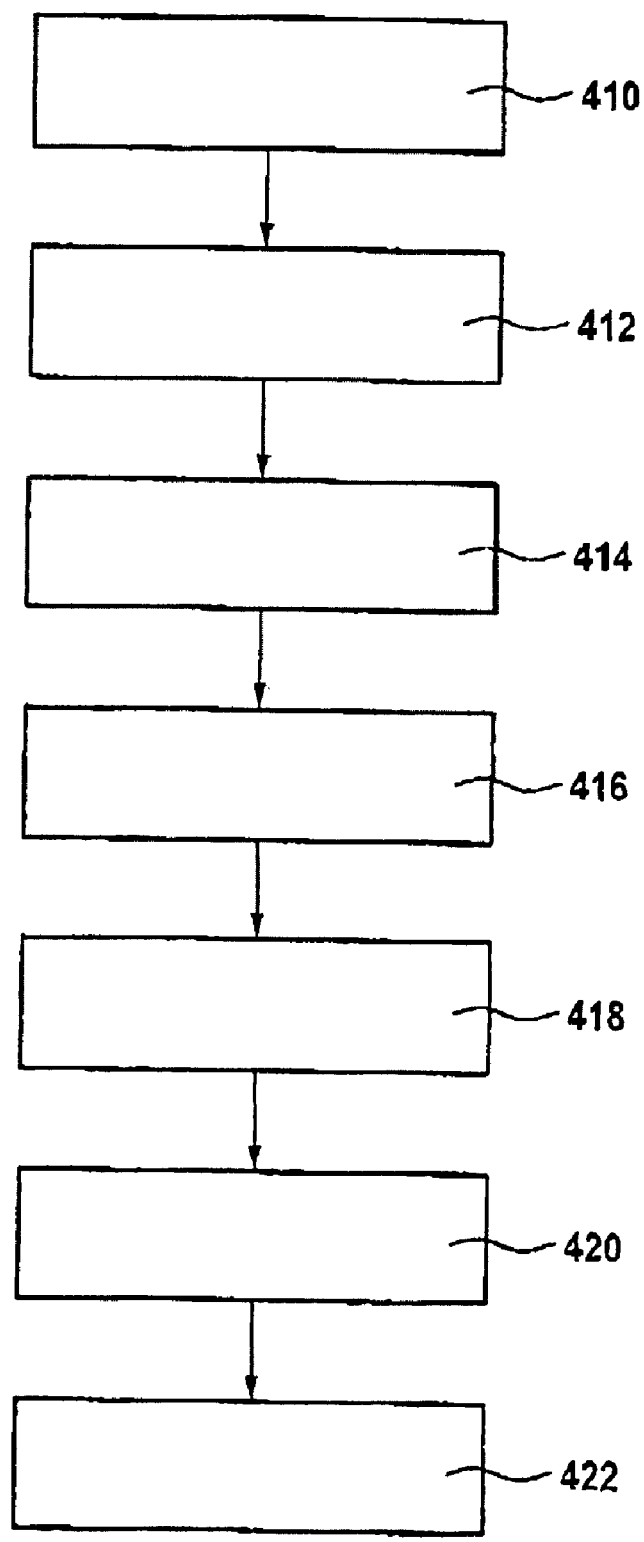
FIG. 4 shows a schematic flowchart of a production method for producing a sensor in accordance with FIG. 1.

FIG. 4 illustrates an exemplary embodiment of a method according to the invention for producing a sensor 110 in accordance with the exemplary embodiment illustrated in FIG. 1. It should be pointed out that other methods can also be used, however, in order to produce the implantable sensor 110 according to the invention in accordance with the illustration in FIG. 1. Moreover, the method steps illustrated need not necessarily be carried out in the order indicated.

In method step 410, the electrode contact layers 114, 116 are applied to a carrier film over a large area. The carrier film need not necessarily be identical with the insulating carrier substrates 112 since said insulating carrier substrates 112 are produced from the carrier film only by later cutting (see below). In this respect, both electrode contact layers 114, 116 and carrier film still have a large area after this first method step 410 has been carried out, such that a large-area "sandwich" of a carrier film, embedded between two electrode contact layers 114, 116, arises. Therefore, the electrode contact layers, too, assume their strip form only after the cutting. By way of example, the layer technologies described above can be used for applying the electrode contact layers 114, 116, including lamination techniques. By way of example, it is possible in this case to use metal films typically having layer thicknesses in the range of a few tens of micrometers. However, depending on the layer technology used, in other embodiments thinner or thicker layers are also conceivable, for example layer thicknesses in the range of a few tens to a few hundreds of nanometers when using a vapor deposition or sputtering method, or layer thicknesses in the region of one hundred micrometers in the case of reel-to-reel lamination methods.

In method step 412 in FIG. 4, the insulator layers 118, 120 are applied. In one embodiment, self-adhesive films can be used, which are in turn applied over a large area to the layered structure produced after step 410 was carried out. In order to produce the openings 126, 128, by way of example said self-adhesive film can be perforated or structured from the outset, but a precise positioning is generally not necessary since the precise positioning of the openings 126, 128 is non-critical in many cases. Lamination methods of this type are known to the person skilled in the art and can be used in diverse ways. The openings 126, 128 can also be introduced subsequently, for example by subsequent cutting and stripping away of the insulator layers 118, 120.

In method step 414 of FIG. 4, the first electrode system 130 is applied. In one embodiment, a Ag/AgCl coating is provided, as described above. In order to apply a Ag/AgCl layer, e.g. a Ag/AgCl paste formed for example by admixing silver and silver chloride particles with a solvent can be introduced into the opening 126 by means of a printing method (e.g. screen printing, pad printing, stencil printing) and/or some other coating method (e.g. blade coating, nozzle coating, in particular by means of slotted nozzles, roll coating, or the like). In one embodiment, the opening 126 is covered substantially completely. Other printing methods can also be used. As shown in FIG. 1, for example, the first electrode system 130 can overlap the first insulator layer 118, which does not disturb the functionality of the common electrode 138. A precise positioning is therefore not necessary. It is even possible for the first insulator layer 118 to be concomitantly coated over a large region.

The second electrode system 132 is subsequently applied in step 416. In one embodiment, a mixture of manganese dioxide and glucose oxidase is provided, as described above. The same method as in method step 414 can be used for application in this case, for example once again a printing method and/or some other coating method. Further methods are also conceivable. In one embodiment, a paste is once again used which is solid after corresponding drying and is therefore insoluble in the surrounding body fluid (electrolyte). Instead of a mixture of manganese dioxide and glucose oxidase, it is also possible firstly to use a pure manganese dioxide, paste onto which glucose oxidase, fort example, is then dispensed after drying.

In method step 418, the hitherto large-area layer construction is produced by a cutting method, e.g. a precision cutting method, whereby strips having the width B (cf. FIG. 1) are produced. In one embodiment, these strips have a longitudinal extent parallel to an insertion direction 150 (cf. FIG. 1). A precise positioning during the precision cutting perpendicular to said insertion direction 150 is not necessary, in contrast to conventional methods, which use structured electrodes in the insertion direction 150 between which the cuts have to be positioned exactly.

In method step 420, the insertion tip 148 is formed onto the insulating carrier substrates 112, that have then been produced. In one embodiment, insertion tips 148 can be produced by simultaneous melting, and drawing, or it is also possible for corresponding hot forming to be effected. In other embodiments, separate tips can be formed onto the insulating carrier substrates 112, such as by fusion with the insulating carrier substrates 112. In yet other embodiments, insertion tips 148 comprise an integrally formed aspect of the substrate 112. Various other possibilities are conceivable. In yet other embodiments, this method step can be omitted because, as mentioned above, the implantable sensor 110 can also be inserted for example into a separate insertion needle. In yet other embodiments, the sensor 110 is provided with its own insertion tip 148, such that the body fluid (electrolyte) washes freely around the electrodes 134, 136.

In method step 422 in FIG. 4, the membrane layer 146 is applied to the sensor 110. In one embodiment, a simple dipping method can be used in which the sensor 110 (without membrane layer) is dipped into a solution or some other liquid containing the membrane material (or a precursor thereof). In other embodiments, a uniform liquid film can optionally additionally be produced by spin-coating, which film can subsequently be dried. A drying step is subsequently carried out, in which the membrane layer 146 dries. A precise positioning of the dipping process is not necessary since it is only necessary to cover the electrodes 134, 136 and more extensive coverage of the sensor 110 is unimportant for the measurement results. As described above, polyurethanes, for example, can be used as materials for the membrane layer 146. In other embodiments, other methods can be used for application, for example methods in which a polymerization does not take place until after the dipping and upon drying, or methods such as spraying methods or printing methods. The membrane materials used should be biocompatible materials, in particular, that is to say materials which, during the measurement duration (typically one week, in some instances also longer, plus a "safety time"), do not conduct any reactions with the surrounding body tissue and/or the body fluid or release toxic substances to an appreciable extent.

Figure 2:
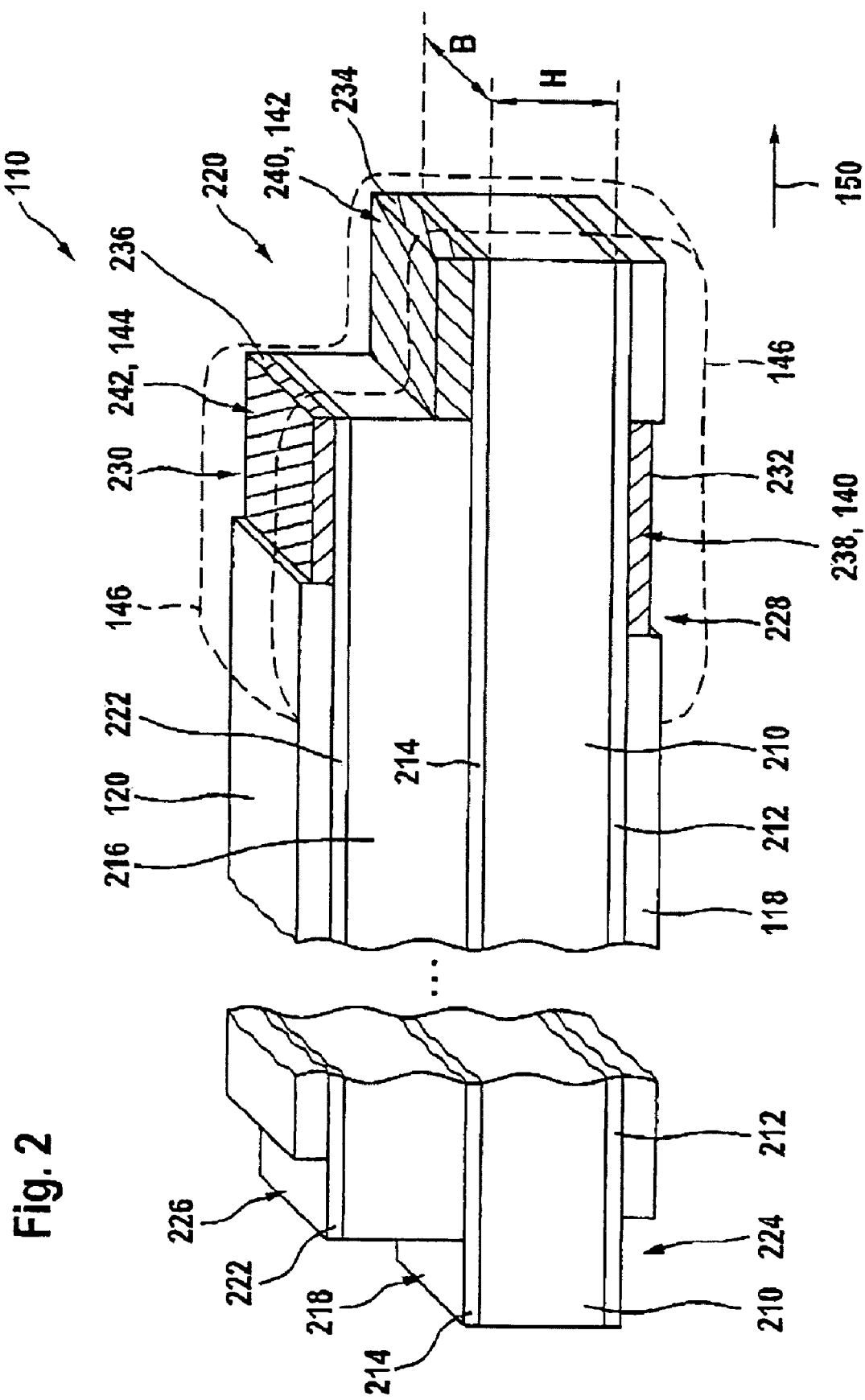
FIG. 2 shows a second exemplary embodiment of a sensor according to the invention.

FIG. 2 illustrates a second exemplary embodiment of an implantable sensor 110 according to the present invention, an insertion tip 148 not being illustrated in this exemplary embodiment. The sensor 110 in accordance with the exemplary embodiment in FIG. 2 has a first insulating carrier substrate 210 layered between a first electrode contact layer 212 and a second electrode contact layer 214. A second insulating carrier substrate 216 is adjacent to the second electrode contact layer 214, but said carrier substrate does not extend over the entire longitudinal extent of the first insulating carrier substrate 210. Thus, at the left-hand end of the sensor 110 as shown in FIG. 2 (that is to say opposite to the insertion direction 150), a region of the second electrode contact layer 214 is left uncovered, such that an electrical contact for making contact with the second electrode contact layer 214 is defined there. At the right-hand end as shown in FIG. 2 (in insertion direction 150), the second insulating carrier substrate 216 ends before the first insulating carrier substrate 210, such that a step 220 is formed in this region. It should be pointed out here that as an alternative, said step 220 can also be formed "towards the bottom" instead of "towards the top" as in FIG. 2, such that overall the layer construction can be inverted.

On the side opposite from the first insulating carrier substrate 210, the second insulating carrier substrate 216 is coated with a third electrode contact layer 222. As shown, all the electrode contact layers 212, 214, 222 once again extend over substantially the entire width B of the sensor 110. The same materials as in the case of FIG. 1 can be used, in principle, as materials for the electrode contact layers 212, 214, 222.

As in FIG. 1 as well, the sensor 110 in accordance with FIG. 2 is also coated on the outside with insulator layers 118, 120, which in this case electrically insulate the first electrode contact layer 212 and the third electrode contact layer 222 on the outside from the surrounding electrolyte, in particular the body fluid. Self-adhesive films may once again be involved in this case. As in FIG. 1 as well, in the example in accordance with FIG. 2, too, the insulators 118, 120 end at the left-hand end of the sensor 110 before the end of the associated insulating carrier substrates 210 and 216, respectively, in such a way that electrical contacts 224, 226 remain free, via which electrical contact can be made with the electrode contact layers 212 and 222, respectively.

Analogously to the embodiment in FIG. 1, in the exemplary embodiment in accordance with FIG. 2, openings 228, 230 are provided in the insulator layers 118 and 120. Said openings 228, 230, which may be formed for example once again as "windows" and/or as simple regions of the electrode contact layers 212, 222 that are exposed, can once again be produced as early as during the application of the insulator layers 118, 120 or can be produced by later structuring.

A first electrode system 232, a second electrode system, 234 and a third electrode system 236 are introduced into the opening 228, applied to the second electrode contact layer 214 in the region of the step 220 and introduced into the opening 230. In one embodiment, a Ag/AgCl layer is used as first electrode system 232 and as second electrode system 234. In other embodiments, a manganese dioxide-GOD layer is provided as third electrode system 232. Together with the associated electrode contact layers, 212, 214 and 222, said electrode systems 232, 234, 236 then respectively form a first electrode 238, a second electrode 240 and a third electrode 242. In this exemplary embodiment, the first electrode 238 acts as a counter electrode 140, the second electrode 240 acts as reference electrode 142 and the third electrode 242 acts as a working electrode 144. Consequently, in this exemplary embodiment in accordance with FIG. 2, the three electrodes 238, 240, 242 are all arranged in different layer planes of the layered construction. Consequently, these electrodes can be made very wide (that is to say over the entire width B in this case), but are nevertheless reliably isolated from one another.

In one embodiment, the sensor 110 is, encapsulated by a membrane layer 146 in the region of the electrodes 238, 240, 242, which membrane layer can be configured analogously to the exemplary embodiment in FIG. 1.

With regard to the layer thickness ratio and the aspect ratio k=H/B, it should be pointed out in this case that the above-mentioned condition is not necessarily intended to apply to the height of an individual insulating carrier substrate 210, 216, but rather preferably to the entire thickness of the layer construction illustrated in FIG. 2. This arises from the fact that, in order to ensure that the sensor 110 is inserted under a patient's skin as far as possible without any bending, the sensor 110 overall should have an approximately square cross section.

Figure 3B:
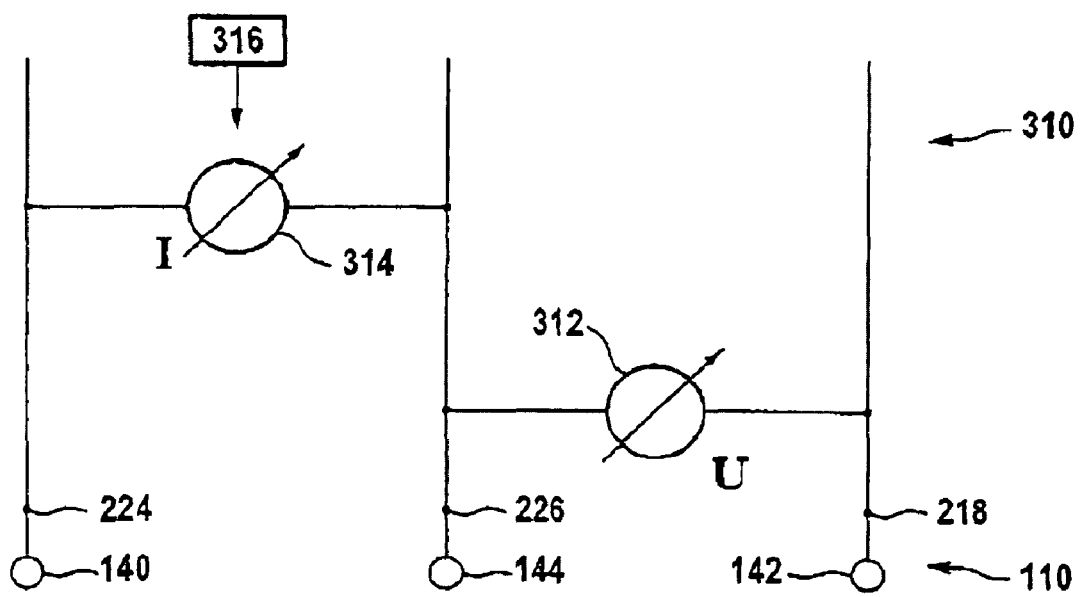
FIG. 3B shows a schematic illustration of a second exemplary embodiment of a device for determining an analyte using a sensor in accordance with FIG. 2.

FIG. 3B illustrates a device 310 for determining a blood glucose concentration using a sensor 110 in accordance with the exemplary embodiment illustrated in FIG. 1. In contrast to the device in accordance with FIG. 3A, the three electrodes 140, 144, 142 are now configured as separate electrodes. The electrolyte of the body fluid once again washes around all three electrodes. At the working electrode 144, which once again has glucose oxidase, a conversion of glucose into gluconolactone with formation of electrons once again takes place. Therefore, the electrochemical potential of the working electrode 144 is once again determined by the concentration of the glucose in the body fluid.

In one embodiment, the device 310 comprises a voltage measuring device 312 for measuring the voltage between working electrode 144 and reference electrode 142 and also a current measuring device 314 for measuring a current flowing between the counter electrode 140 and the working electrode 144. In other embodiments, a control device 316 is provided, which controls the current flowing between counter electrode 140 and working electrode 144 in such a way that the voltage between working electrode 144 and reference electrode 142 reaches a predetermined desired value. Generally, the device functions as described with reference to FIG. 3A.

Figure 5:
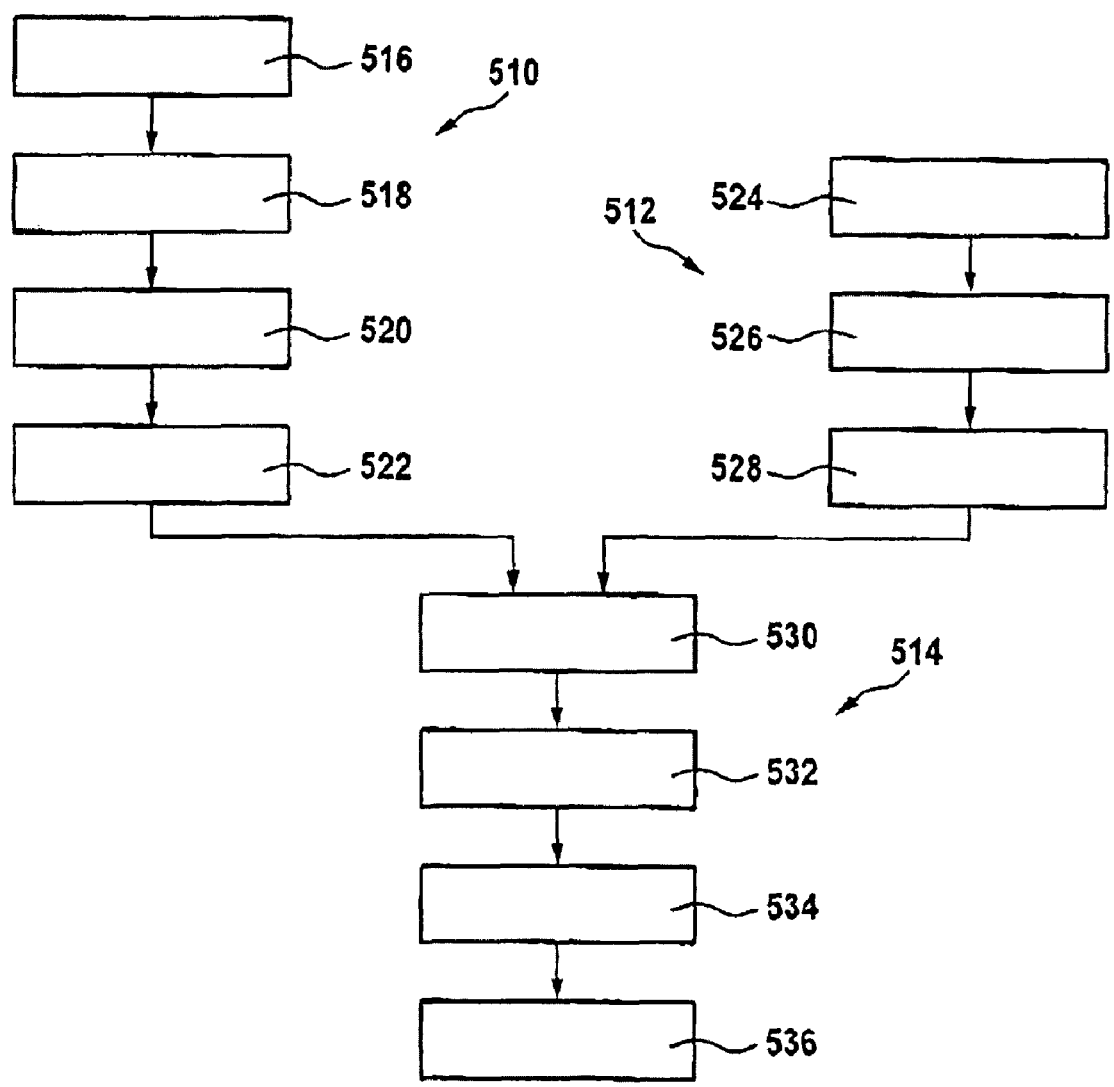
FIG. 5 shows a schematic flowchart of a production method for producing a sensor in accordance with FIG. 2.

Finally, FIG. 5 illustrates an exemplary embodiment according to the invention of a production method for the production of a sensor 110 in accordance with the exemplary embodiment, in FIG. 2. It should once again be pointed out, however, that other production methods for the production of said sensor 110 can also be used. Moreover, the method steps can once again be carried out in a different order, and once again it is also possible to carry out additional method steps that are not described herein.

Instead of a layer-by-layer construction "from the bottom towards the top", the method in FIG. 5 is divided into two partial methods in which a first partial layer construction (partial method 510) and a second partial layer construction (partial method 512) are produced independently of one another. The two partial layer constructions are subsequently joined together and processed further in the common method 514.

In the partial method 510, firstly in step 516, a first carrier film is coated with the electrode contact layers 212, 214 over a large area. On one side of the layered construction thus produced, in step 518, the insulator film 118 is applied to the first electrode contact layer 212, analogously to method step 412 in accordance with FIG. 4, but only on one side.

In step 520, the first electrode system 232 is introduced into the opening 228 in the insulator layer 118 for example by means of the method described with reference to FIG. 4.

In step 522, the second electrode system 234 is applied to a region of the second electrode contact layer 214 in which the step 220 is formed later. As an alternative, the second electrode system 234 can be applied for example only in the context of the common method 514, that is to say after the two partial layer constructions have been joined together (see below).

After method steps 516 to 522 have been carried out, the first partial layer construction is finished. A second partial layer construction is produced in method steps 524 to 528 (in particular independently of the above method steps, that is to say in parallel, for example). For this purpose, firstly in method step 524 a second carrier film is coated with the third electrode contact layer 222 over a large area and on one side. In method step 526, the insulator layer 120 is applied to the third electrode contact layer 222, leaving an opening 230 remaining. For the techniques and materials of the application of the individual layers, reference should once again be made to the exemplary embodiments in accordance with the description corresponding to FIG. 4.

In method step 528 of the partial method 512, the third electrode system 236 is introduced into the opening 230. This means that the second partial method 512 is finished, and the second partial layer construction has been produced.

In the common method 514, in method step 530, the second partial layer construction composed of the second carrier film, the third electrode contact layer 222, the insulator layer 120 and the third electrode system 236 is applied to the first partial layer construction composed of the insulator layer 118, the first electrode contact layer 212, the first carrier film, the second electrode contact layer 214 and the first electrode system 232 and the second electrode system 234. By way of example, lamination techniques can once again be used for this application.

In subsequent method step 532, cutting once again takes place, in which the hitherto large-area layer constructions are cut into strip-type sensors 110. In this case once again, as described above, exact positioning is not absolutely necessary.

In method step 534, an insertion tip 148 is optionally formed onto the layer construction, said insertion tip not being represented in the illustration in accordance with FIG. 2. In method step 536, the membrane layer 146 is applied, analogously to method step 422, for example once again by means of a dipping method.

The exemplary methods for producing the sensors 110 as illustrated in FIGS. 4 and 5 can be realized well on an industrial scale. Thus, reel-to-reel methods can be used, in particular, for which automatic machines are available from other areas of technology, such that special manufacturing of costly production equipment is not necessary. The method is extremely cost-effective and can be conducted with a high yield and high throughput.

Figure 6:
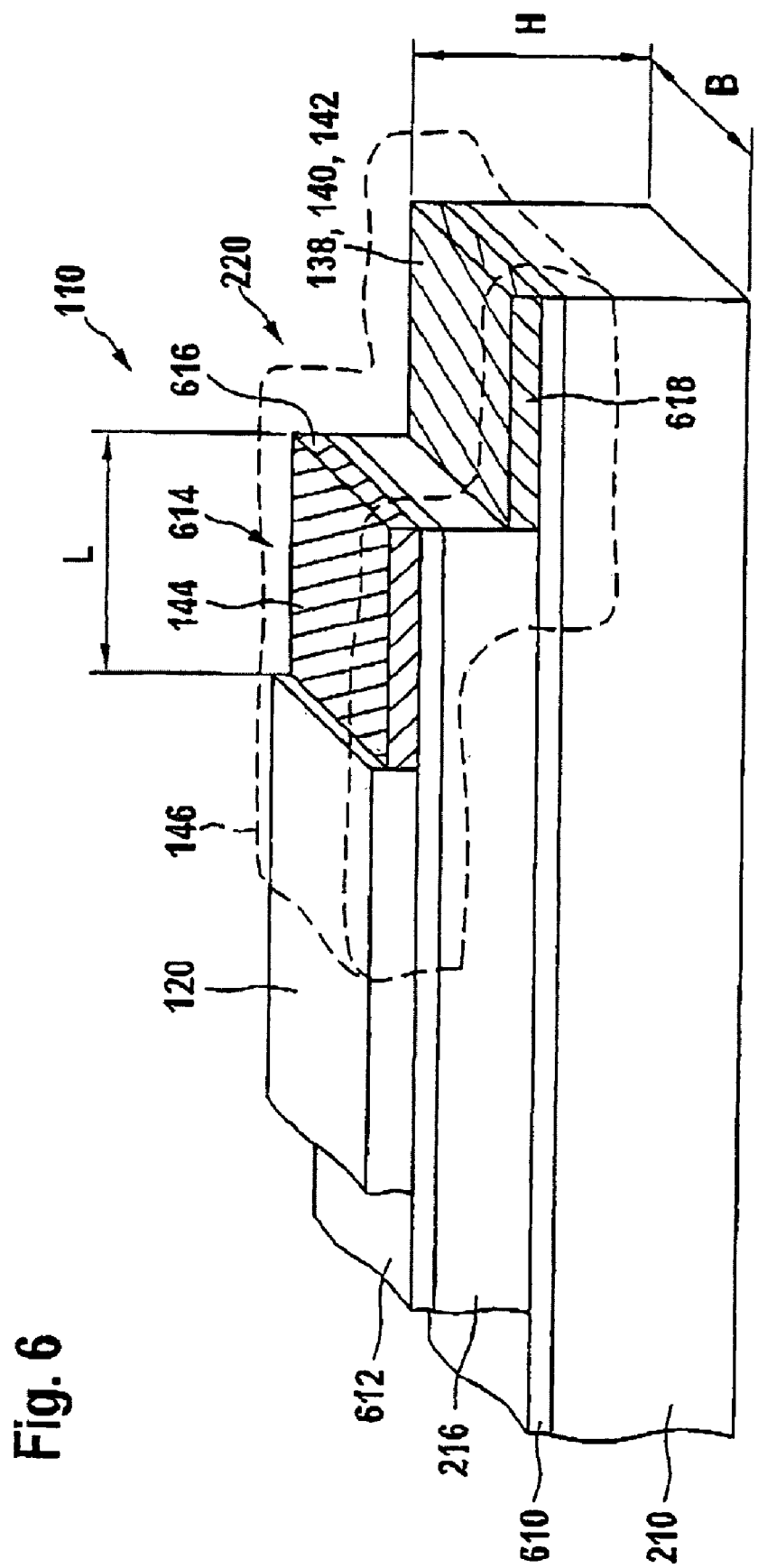
FIG. 6 shows a third exemplary embodiment of an implantable sensor with a step arrangement and a common electrode.
Figure 7:
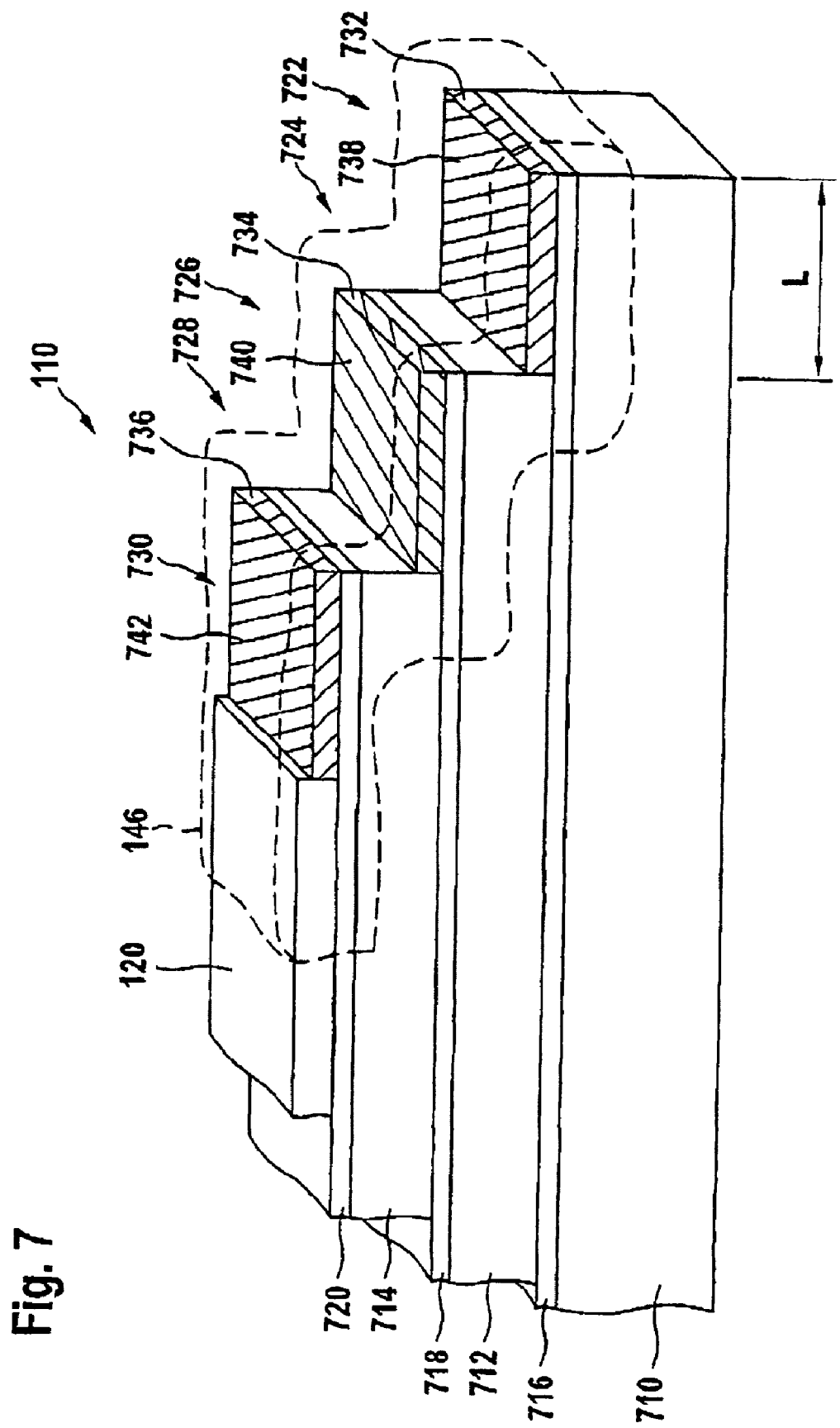
FIG. 7 shows a fourth exemplary embodiment of an implantable sensor with two steps and three electrodes.
Figure 8:
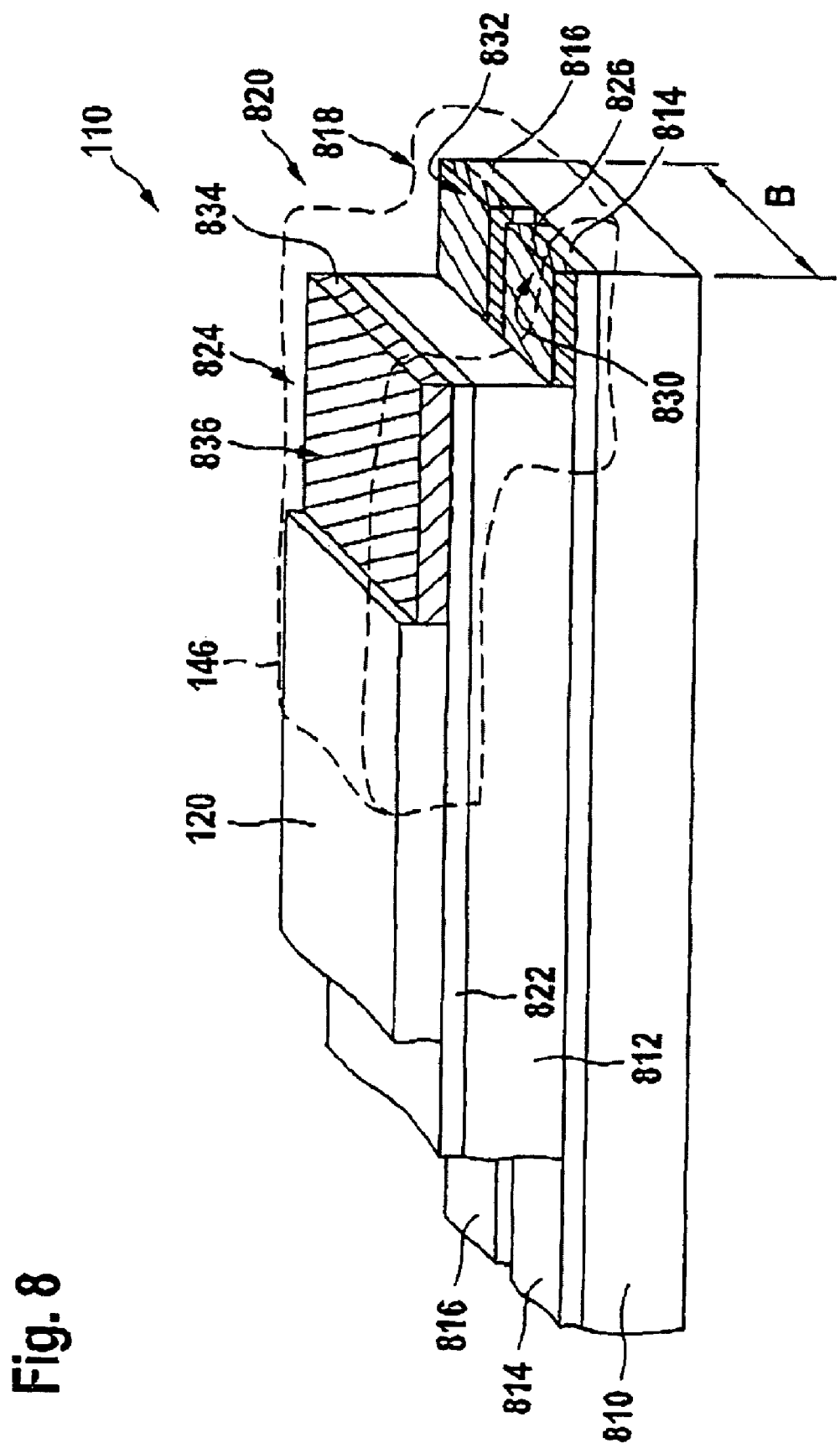
FIG. 8 shows a fifth exemplary embodiment of an implantable sensor with one step and three separate electrodes.

FIGS. 6 to 8 illustrate other embodiments of implantable sensors 110 according to the present invention. FIG. 6 shows an exemplary embodiment of an implantable sensor 110 illustrated in a step arrangement. The implantable sensor 110 once again has a first insulating carrier substrate 210, on which a first electrode contact layer 610 is applied. By way of example, said first insulating carrier substrate 210 may have a layer thickness of approximately 200 μm. A first electrode contact layer 610 is applied to said first insulating carrier substrate 210, analogously to the previous exemplary embodiments, in which case a layer of gold or a layer of some other metal or conductive polymer may once again be involved. Said first electrode contact layer has a layer thickness of a few μm, for example.

A second insulating carrier substrate 216 is applied to the first electrode contact layer 610, and can be configured analogously to the first insulating carrier substrate 210. In this case, on the electrode side, i.e. on the right-hand side in FIG. 6, the second insulating carrier substrate 216 does not extend over the entire length of the first insulating carrier substrate 210, such that a step 220 arises in this region. A second electrode contact layer 612 is applied to the second insulating carrier substrate 216, and can be configured analogously to the first electrode contact layer 610. An insulator layer 120, for example an adhesive tape, is once again applied to the second electrode contact layer, analogously to the previous exemplary embodiments. On the electrode side (i.e. once again on the right-hand side of the implantable sensor 110 in FIG. 6), said insulator layer 120 does not extend over the entire length of the second insulating carrier substrate 216 and the second electrode contact layer 612, such that once again, analogously to the opening 230 in FIG. 2, an opening 614 remains, that is to say a region in which the second electrode contact layer 612 is not covered by the insulator layer 120.

In this region of the opening 614, the second electrode contact layer 612 is covered with a first electrode system 616, in one embodiment comprising a $MnO_2/C$ (manganese dioxide) layer mixed with GOD. Overall, a working electrode 144 is thus formed in the region of the opening 614.

The first electrode contact layer 610, which is not covered by the second insulating carrier substrate 216 in the region of the step 220, is covered. In said region by a second electrode system 618, which can be configured for example analogously to the first electrode system 130 in accordance with the exemplary embodiment in FIG. 1. In one embodiment, the second electrode system 618 comprises a Ag/AgCl coating. Consequently, a common electrode 138 performing the functions of counter electrode 140 and reference electrode 142 is formed from the second electrode system 618 and the first electrode contact layer 610, in the region of the step 220. Working electrode 144 and common electrode 138 are once again coated by a membrane layer 146, analogously to the previous exemplary embodiments.

The exemplary embodiment of the implantable sensor 110 in accordance with FIG. 6 therefore represents a mixed form of the exemplary embodiments in accordance with FIGS. 1 and 2. On the one hand, a step arrangement in accordance with the exemplary embodiment in FIG. 2 is provided, in which-both electrodes 144, 138 are arranged parallel and point in the same direction with their free electrode areas (upward in the exemplary embodiment in accordance with FIG. 6). At the same time, the counter electrode 140 and the reference electrode 142 are configured as a common electrode 138, analogously to the exemplary embodiment in FIG. 1. In, one embodiment, the width B of the implantable sensor 110 in accordance with the exemplary embodiment in FIG. 6 is approximately 1 mm. This results, taking account of the height H of the insulating carrier substrate 210 and 216, in an overall height (approximately 2H) to width (b) ratio of about 0.4. In other embodiments, the electrodes 144, 138 have a length L of approximately 1 mm.

FIG. 7 illustrates a further exemplary embodiment of an implantable sensor 110, which once again represents a modification of the exemplary embodiment in accordance with FIG. 2. The implantable sensor 110 in accordance with FIG. 7 has three insulating carrier substrates 710, 712 and 714, the latter once again being covered by associated electrode contact layers 716, 718 and 720. In this case, the second insulating carrier substrate 712 and the second electrode contact layer 718 are once again applied to the first insulating carrier substrate 710 and the first electrode contact layer 716 in such a way that a first opening 722 remains and a first step 724 is formed. The third insulating carrier substrate 714 and the third electrode contact layer 720 are analogously applied to the second insulating carrier substrate 712 and the second electrode contact layer 718 in such a way that a second opening 726 is defined, as well as a second step 728. In addition, an insulator layer 120 is once again applied to the third electrode contact layer 720, said insulator layer once again not extending completely as far as the electrode-side end of the third electrode contact layer 720, such that a third opening 730 remains. In the region of the three openings 722, 726 and 730, the electrode contact layers 716, 718 and 720 are respectively covered with electrode systems 732, 734 and 736. In one embodiment, the first electrode system 732 and the third electrode system 736 each comprise, Ag/AgCl coatings. In other embodiments, the second electrode system 734 comprises a $MnO_2/C$ (manganese dioxide) layer. Accordingly, a reference electrode 738, a working electrode 740 and a counter electrode 742 are formed in the different layer planes of the "stair structure" in accordance with FIG. 7. Consequently, the layer construction of the exemplary embodiment of the implantable sensor 110 in accordance with FIG. 7 corresponds, in principle, to the layer construction in FIG. 2, but with the difference that all the electrodes 738, 740, 742 point in one direction with their electrode surfaces. In this case, the working electrode 740 is "framed" between the reference electrode 738 and the counter electrode 742. The electrodes 738, 740, 742 are once again encapsulated by a membrane layer 146. The layer thicknesses of the insulating carrier substrates 710, 712, 714 correspond to the layer thickness H of the insulating carrier substrate 210 in accordance with FIG. 6. In one embodiment, thickness H is approximately 200 μm. In other embodiments, the electrode contact layers 716, 718 and 720 have a thickness of approximately 50 μm, in the same way as the electrode systems 732, 734 and 736. In yet other embodiments, the length L of the individual openings 722, 726 and 730 is approximately 1 mm.

FIG. 8 illustrates a further exemplary embodiment of an implantable sensor 110, which combines properties of the implantable sensors in accordance with the exemplary embodiments in FIGS. 6 and 7. Thus, two insulating carrier substrates 810 and 812 are once again provided, analogously to FIG. 6. In contrast to FIG. 6, however, rather than an individual electrode contact layer, two electrode contact layers 814 and 816 are applied to the first insulating carrier substrate 810, said electrode contact layers each taking up approximately half the width B of the first insulating carrier substrate 810 and extending along the length of said first insulating carrier substrate 810. This can be effected in terms of production technology for example by a large-area electrode contact layer firstly being applied to the first insulating carrier substrate 810 in order subsequently to electrically isolate and mechanically separate this large-area electrode contact layer into the two individual electrode contact layers 814 and 816 by means of a cutting method or a laser ablation method, for example. As an alternative, the two electrode contact layers 814, 816 can also be applied to the first insulating carrier substrate 810 directly, that is to say in a manner already electrically insulated from one another. The second insulating carrier substrate 812 is once again applied to the two electrode contact layers 814, 816 or the first insulating carrier substrate 810 in such a way that, at the electrode-side end (on the right in FIG. 8), a first opening 818 remains and a step 820 is formed.

A third electrode contact layer 822 is applied to the second insulating carrier substrate, said electrode contact layer, analogously to FIG. 6, once again being covered by an insulator layer 120 in such a way that a second opening 824 remains at the electrode-side end (on the right in FIG. 8).

In the region of the first opening 818, the first electrode contact layer 814 is covered with a first electrode system 826, and the second electrode contact layer 816 is covered with a second electrode system 828. In one embodiment, both electrode, systems 826, 828 comprise Ag/AgCl coatings. Consequently, a counter electrode 830 and a reference electrode 832 are formed which can once again be used for example in a device 310 in accordance with the exemplary embodiment in FIG. 3B. In other embodiments, in the second opening 824, a $MnO_2/C$ (manganese dioxide) layer is applied as third electrode system 834 to the third electrode contact layer 822, such that a working electrode 836 is formed here.

It can thus be established that the exemplary embodiment of the implantable sensor 110 in accordance with FIG. 8 has, in principle, a "one-step construction" similar to FIG. 6, but a common electrode 136 is not used. Rather, counter electrodes 830 and reference electrode 832 lie separately in a plane of the layer construction. Accordingly, a device 310 in accordance with FIG. 3B is used as an example, whereas a device 310 in accordance with the exemplary embodiment in FIG. 3A could be used, for example, for the exemplary embodiment of the implantable sensor 110. Analogously, the device 310 in accordance with the exemplary embodiment in FIG. 3B could also be used for the exemplary embodiment in FIG. 7.

Analogously to the exemplary embodiments in FIGS. 6 and 7, in one embodiment in accordance with FIG. 8 the implantable sensor 110 is coated completely or partly with a membrane layer 146 in the region of the electrodes 830, 832 and 836. What is common to all three exemplary embodiments in accordance with FIGS. 6 to 8 is that all the electrodes lie parallel, (albeit in different layer planes) and point in the same direction with their large-area electrode surface.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which, a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An implantable sensor for determining a concentration of at least one analyte in a body tissue or a body fluid, the implantable sensor having a layered construction comprising at least one insulating carrier substrate and at least two electrodes which are arranged in at least two different layer planes of the implantable sensor, are electrically isolated from one another by the at least one insulating carrier substrate and have electrode areas, the electrode areas facing the medium when the sensor has been implanted, and being in contact directly or via a generally analyte-permeable membrane layer with the body tissue or body fluid over a large area and substantially uniformly, the implantable sensor further comprising at least two electrode contact layers in electrical contact respectively with the at least two electrodes, wherein the at least one insulating carrier substrate has a width, and the at least two electrodes or the at least two electrode contact layers extending over at least 80% of the entire width of the at least one insulating carrier substrate.

2. The implantable sensor according to claim 1 wherein the at least two electrodes comprise at least one working electrode and at least one further electrode comprising at least one of a counter electrode and a reference electrode, the at least one working electrode and the at least one further electrode being arranged in different planes of the layered construction.

3. The implantable sensor according to claim 2 wherein the at least one further electrode comprises a common electrode comprising a counter electrode and a reference electrode.

4. The implantable sensor according to claim 1 wherein the at least two electrode contact layers are covered at least partly with respect to the body tissue or body fluid by at least one insulator layer.

5. The implantable sensor according to claim 4 wherein the at least one insulator layer comprises a self-adhesive film layer.

6. The implantable sensor according to claim 1 wherein the at least one membrane layer comprises a polyurethane.

7. The implantable sensor according to claim 1 wherein the at least one carrier substrate is generally analyte-impermeable.

8. The implantable sensor according to claim 1 wherein the at least one carrier substrate comprises an insulating polymer.

9. The implantable sensor according to claim 8 wherein the insulating polymer comprises a polyester.

10. The implantable sensor according to claim 1 further comprising an insertion tip configured for inserting the implantable sensor into the body tissue or body fluid.

11. The implantable sensor according to claim 10 wherein the at least one insulating carrier substrate and/or the implantable sensor has a width B and a height H, the ratio H/B or the reciprocal thereof defining an aspect ratio k, the aspect ratio k being at least about 0.3.

12. The implantable sensor according to claim 11 wherein aspect ratio k is at least about 0.5.

13. The implantable sensor according to claim 11 wherein aspect ratio k is at least about 0.9.

14. The implantable sensor according to claim 1 wherein the layered construction, comprises a stepped layer construction comprising at least two insulating carrier substrates forming at least one step.

15. The implantable sensor according to claim 14 wherein one of the at least two electrically isolated electrodes is arranged in the plane of the at least one step, and wherein said one electrode and another of the at least two electrically isolated electrodes comprise generally parallel, equidirectional electrode areas.

16. The implantable sensor according to claim 14, the stepped construction comprising two steps each comprising equidirectional electrodes arranged in the planes of the respective two steps.

17. The implantable sensor according to claim 14 wherein at least one further electrode is provided which is arranged on a side of the at least one carrier substrate that is remote from the at least one step, and is oriented with its electrode area opposite to the step.

18. The implantable sensor according to claim 1 wherein at least two electrodes are arranged on opposite sides of the at least one carrier substrate and have oppositely directed electrode areas facing the body tissue or body fluid.

19. The implantable sensor according to claim 1 wherein a back-to-back construction, having at least one carrier substrate provided between a first electrode contact layer and a second electrode contact layer, at least one first electrode being provided on that side of the first electrode contact layer which is remote from the at least one carrier substrate, and at least one second electrode being provided on that side of the second electrode contact layer which is remote from the carrier substrate.

20. The method according to claim 1, wherein the at least two electrodes or the at least two electrode contact layers extend at least 95% of the entire width of the at least one insulating carrier substrate.

21. The method according to claim 1, wherein the at least two electrodes or the at least two electrode contact layers extend the entire width of the at least one insulating carrier substrate.

22. A device for determining a concentration of at least one-analyte in a body tissue or a body fluid, comprising at least one implantable sensor according to claim 2, the further electrode comprising at least one counter electrode and at least one reference electrode, and further comprising at least one voltage measuring device for measuring a voltage between the at least one working electrode and the at least one reference electrode of the implantable sensor.

23. The device according, to claim 22, further comprising at least one current measuring device for measuring a current between the at least one counter electrode and the at least one working electrode of the implantable sensor.

24. The device according to claim 22 wherein the device is configured for continuously determining a concentration of at least one analyte in the body tissue or body fluid.

25. An implantable sensor for determining a concentration of at least one analyte in a body tissue or a body fluid, the implantable sensor having a layered construction comprising at least one insulating carrier substrate and at least two electrodes which are arranged in at least two different layer planes of the implantable sensor, are electrically isolated from one another by the at least one insulating carrier substrate and have electrode areas, the electrode areas facing the medium when the sensor has been implanted, and being in contact directly or via a generally analyte-permeable membrane layer with the body tissue or body fluid over a large area and substantially uniformly, the implantable sensor further comprising at least two electrode contact layers in electrical contact respectively with the at least two electrodes, wherein the at least one insulating carrier substrate has a width defined by two spaced edges of the carrier substrate, and wherein at least one of the two electrodes and at least one of the two electrode contact layers extend substantially to the two edges of the carrier substrate.

26. The implantable sensor of claim 25, wherein at least one of the two electrodes comprises an enzyme.

27. An implantable sensor for determining a concentration of at least one analyte in a body tissue or a body fluid, the implantable sensor having a layered construction comprising at least one insulating carrier substrate and at least two electrodes which are arranged in at least two different layer planes of the implantable sensor, are electrically isolated from one another by the at least one insulating carrier substrate and have electrode areas, the electrode areas facing the medium when the sensor has been implanted, and being in contact directly or via a generally analyte-permeable membrane layer with the body tissue or body fluid over a large area and substantially uniformly, the implantable sensor further comprising at least two electrode contact layers in electrical contact respectively with the at least two electrodes, wherein the at least one insulating carrier substrate has a width defined by two spaced edges of the carrier substrate, and wherein one of the at least two electrodes extends over substantially the entire width of the carrier substrate and includes an enzyme.

28. The implantable sensor of claim 27, wherein at least one of the two electrode contact layers extends over substantially the entire width of the carrier substrate.

29. An implantable sensor for determining a concentration of at least one analyte in a body tissue or a body fluid, the implantable sensor having a layered construction comprising at least one insulating carrier substrate and at least two electrodes which are arranged in at least two different layer planes of the implantable sensor, are electrically isolated from one another by the at least one insulating carrier substrate and have electrode areas, the electrode areas facing the medium when the sensor has been implanted, and being in contact directly or via a generally analyte-permeable membrane layer with the body tissue or body fluid over a large area and substantially uniformly, the implantable sensor further comprising at least two electrode contact layers in electrical contact respectively with the at least two electrodes, wherein the at least one insulating carrier substrate has a width defined by spaced edges of the carrier substrate, and wherein at least one of the two electrodes extends 100% to the edges of the carrier substrate.

30. The implantable sensor of claim 29, wherein at least one of the two electrode contact layers extends 100% to the edges of the carrier substrate.

* * * * *

UNITED STATES PATENT AND TRADEMARK OFFICE
CERTIFICATE OF CORRECTION

PATENT NO. : 8,326,393 B2  
APPLICATION NO. : 12/142437  
DATED : December 4, 2012  
INVENTOR(S) : Holger Kotzan et al.

Page 1 of 1

It is certified that error appears in the above-identified patent and that said Letters Patent is hereby corrected as shown below:

Column 24, line 45 (Claim 20, line 1) the word [method] is replaced with --implantable sensor--.

Column 24, line 49 (Claim 21, line 1) the word [method] is replaced with --implantable sensor--.

Signed and Sealed this  
Twenty-sixth Day of February, 2013

Teresa Stanek Rea  
*Acting Director of the United States Patent and Trademark Office*